(12) United States Patent
Myntti (10) Patent No.: US 11,090,369 B2
(45) Date of Patent: Aug. 17, 2021

(54) ANTIMICROBIAL COMPOSITIONS AND METHODS EMPLOYING SAME

(71) Applicant: Next Science IP Holdings Pty Ltd, Chatswood (AU)

(72) Inventor: Matthew F. Myntti, St. Augustine, FL (US)

(73) Assignee: Next Science IP Holdings Pty Ltd, Chatswood (AU)

( * ) Notice: Subject to any disclaimer, the term of this patent is extended or adjusted under 35 U.S.C. 154(b) by 259 days.

(21) Appl. No.: 16/314,168

(22) PCT Filed: Jun. 28, 2017

(86) PCT No.: PCT/US2017/039836
§ 371 (c)(1),
(2) Date: Dec. 28, 2018

(87) PCT Pub. No.: WO2018/005702
PCT Pub. Date: Jan. 4, 2018

(65) Prior Publication Data
US 2019/0262433 A1    Aug. 29, 2019

Related U.S. Application Data

(60) Provisional application No. 62/524,522, filed on Jun. 24, 2017, provisional application No. 62/357,147, filed on Jun. 30, 2016.

(51) Int. Cl.
| | | |
|---|---|---|
| *A61K 38/47* | (2006.01) |
| *A61P 31/04* | (2006.01) |
| *A61K 9/00* | (2006.01) |
| *A61K 9/08* | (2006.01) |
| *A61K 47/10* | (2017.01) |
| *A61K 47/12* | (2006.01) |
| *A61K 47/20* | (2006.01) |
| *A01N 63/00* | (2020.01) |
| *A01N 37/02* | (2006.01) |

(52) U.S. Cl.
CPC .............. *A61K 38/47* (2013.01); *A01N 37/02* (2013.01); *A01N 63/00* (2013.01); *A61K 9/0043* (2013.01); *A61K 9/0046* (2013.01); *A61K 9/08* (2013.01); *A61K 47/10* (2013.01); *A61K 47/12* (2013.01); *A61K 47/20* (2013.01); *A61P 31/04* (2018.01); *C12Y 302/01017* (2013.01)

(58) Field of Classification Search
CPC ..................... C12N 9/2402; C12Y 302/01017
See application file for complete search history.

(56) References Cited

FOREIGN PATENT DOCUMENTS

| WO | WO 2007/134055 | * 11/2007 |
| WO | WO 2008/070387 | * 6/2008 |
| WO | WO 2010/011605 | * 1/2010 |

* cited by examiner

*Primary Examiner* — Thane Underdahl
(74) *Attorney, Agent, or Firm* — David G. Burleson (57) ABSTRACT

A composition that can be used to treat a wide spectrum of gram positive and gram negative bacteria, including but not limited to those in biofilm form, and other microbes can be used in cilia-containing areas such as the sinus cavities and middle/inner ear, while resulting in no, or very minimal amounts of, deciliation. Where such a targeted treatment area includes a biofilm, the composition often can detach and assist in removing the biofilm from affected tissue. Many embodiments of the composition are biocompatible.

20 Claims, 6 Drawing Sheets

FIG. 8

ANTIMICROBIAL COMPOSITIONS AND METHODS EMPLOYING SAME

CROSS-REFERENCE TO RELATED APPLICATIONS

This is a national stage entry of international application PCT/US2017/039836 which claims priority to U.S. provisional patent application nos. 62/357,147, filed 30 Jun. 2016, and 62/524,522, filed 24 Jun. 2017, which are incorporated herein by reference.

BACKGROUND INFORMATION

Microbes are found virtually everywhere, often in high concentrations, and are responsible for a significant amount of disease and infection. Eliminating these microorganisms from targeted tissues is often desirable and sometimes critically important.

Bacteria present special challenges because they can exist in a number of forms, including planktonic, spore and biofilm, and their various self-preservation mechanisms make treating and/or eradicating them extremely difficult. For example, the bacteria in biofilms or spores are down-regulated (sessile), making them resistant to attack by a large group of antibiotics and antimicrobials that are effective only during the active parts of a bacterium's lifecycle, e.g., cell division.

In a biofilm, microbes such as bacteria or fungi interact with and adhere to surfaces, forming colonies which facilitate continued growth. The microbes produce exopolysaccharide (EPS) and/or extracellularpolysaccharide (ECPS) macromolecules that keep them attached to a surface and form a protective barrier effective against many forms of attack. The small diameter of flow channels in the EPS/ECPS macromolecular matrix, which restricts the size of molecules that can reach the underlying microbes, and consumption of biocides through interactions with portions of the EPS/ECPS macromolecular matrix and microbe secretions and waste products contained therein probably play roles in the protective barrier function.

Due to the protection afforded by the macromolecular matrix and their down-regulated state, microbes in a biofilm state are very difficult to treat. The types of biocides and antimicrobials effective in treating microbes in this form often are strongly acidic or caustic, and often oxidizing due to the presence of halogen atoms, oxygen atoms, or both. Large dosages of such chemicals must be allowed to contact the biofilm for extended amounts of time to be effective, which makes them impractical for many applications.

Compositions intended for use in connection with compromised animal/human tissue which solvate a biofilm matrix so that it can be rinsed or otherwise removed from infected tissue have been described in, e.g., U.S. Pat. Nos. 7,976,873, 7,976,875, 7,993,675, and 7,959,943. Compositions based on similar components but intended for other uses have been described in U.S. Pat. Nos. 8,940,792 and 9,314,017 and U.S. Pat. Publ. Nos. 2010/0086576, 2014/0242188, and 2016/0073628.

However, animal testing has shown that compositions such as those described in the preceding paragraph, when applied to ciliated tissue such as exist in the sinus cavities and inner ear, tend to result in deciliation, i.e., the loss in functionality and/or removal of cilia, which are the relatively thick protruding organelles found in and projecting from the body of eukaryotic cells. Sinus cavity cilia facilitate clearance of the sinuses, while those in the ear act as sound receptors.

Testing suggests that contributing factors in deciliation likely include the presence of ionic surfactants, high effective solute concentrations, and pH. Unfortunately, compositions described in the documents listed in the preceding paragraph all call for at least 0.2% (w/w) surfactant, and many require or prefer low pH and very high effective solute concentrations, i.e., osmolarities.

Because biofilms deciliate affected tissue anyway and because cilia in the sinus cavities can regrow within days, limited deciliation which does not impede clearing of the sinuses might be an acceptable side effect in a product intended for use in those sinus cavities not connected to the inner ear via a Eustachian tube. However, compositions intended for use in treating portions of the ear inward of the tympanic membrane (or treating a sinus cavity that is connected to the inner ear) cannot be permitted to result in deciliation because inner ear cilia do not regrow, resulting in irreparable hearing loss.

That which is desirable is a composition that can effectively treat microbes present in cilia-containing areas such as the sinus cavities and middle/inner ear, particularly microbes in a biofilm form, without resulting in unacceptable levels of deciliation. A composition that can accomplish the foregoing while also causing or facilitating detachment of biofilms from affected tissue is particularly desirable.

Such an antimicrobial composition that can be provided in a variety of viscosities and introduced to the targeted area via more than one delivery route is particularly desirable.

Further desirable is a composition that is sufficiently biocompatible so as to not require removal via irrigation using, for example, a saline rinse.

SUMMARY

The present invention is directed to compositions that can be used to treat microbes including but not limited to bacteria, including those in biofilm form. The term "treat" includes killing, inactivating and/or removal.

A composition according to the present invention is effective against a wide spectrum of gram positive and gram negative bacteria and exhibits lethality toward other microbes such as viruses, fungi, molds, and yeasts.

Advantageously, this composition can effectively kill microbes present in cilia-containing areas such as the sinus cavities and middle/inner ear, even microbes in a biofilm form, while resulting in no, or very minimal amounts of, deciliation. Where such a targeted treatment area includes a biofilm, the composition often can detach and assist in removing the biofilm from affected tissue.

The composition typically is provided as a liquid having a viscosity similar to that of water, but can be thickened to provide a variety of forms with a range of viscosities. It also can be delivered via techniques employing a variety of presently available equipment.

All embodiments of the composition are biocompatible, while many embodiments are ciliacompatible.

The composition has a near-neutral pH, typically from 6 to 8, and includes a moderate amount of osmotically active solutes, often having an effective solute concentration of no more than 400 mOsm/L, commonly no more than 250 mOsm/L and more commonly no more than 200 mOsm/L. Embodiments intended for use in the sinus cavities can include no more than 1.0, 0.8, 0.7 or 0.5% (w/v) of one or more anionic surfactants, while other embodiments intended for use in the middle or inner ear can include no added surfactant(s). The composition includes at least 2% (w/v) of one or more non-aqueous liquids, with the upper limit determined in large part by the intended end use of the composition. The composition also includes at least 0.005% (w/v) of one or more enzymes which are active at 6≤pH≤8 so as to facilitate microbial cell wall rupture by catalyzing and/or easing the breaking of chemical bonds present in or between molecules in those cell walls. (Because enzymes vary so widely in terms of chemical structure and targeted utility, the upper limit often is based on the amount of a particular enzyme, if any, that results in a level of ciliotoxicity deemed to be unacceptable for a particular end use.)

The composition is effective at interrupting or breaking ionic crosslinks in the macromolecular matrix of a biofilm, which facilitates passage of the solutes, surfactant (if present) and enzyme through the matrix to the microbes (e.g., bacteria) entrained therein and/or protected thereby. The composition thus bypasses and/or disables the biofilm defenses, allowing previously protected microbes to be accessed and killed, typically by processes that include inducing membrane leakage in bacteria, leading to cell lysis.

Also provided are methods for treating affected areas including application of non-solid compositions can be applied to an affected area. The composition can be non-flowing if intended to be left in place or can be a liquid if intended to irrigate or otherwise flow over or around a treatment area.

Embodiments of the composition can be used to treat chronic otitis media, cholesteatoma and other bacterial ear conditions, as well as chronic rhinosinusitis and other bacterial sinus conditions.

Often, a flowable form of the composition is introduced peri- or post-surgery performed on an affected area. For example, a composition can be introduced into the middle ear via a tympanostomy tube immediately or soon after its insertion or, if deemed necessary desirable, during a post-surgical follow-up evaluation.

To assist in understanding the following description of various embodiments, certain definitions are provided immediately below. These are intended to apply throughout unless the surrounding text explicitly indicates a contrary intention:

"comprising" means including but not limited to those ingredients which follow the term;

"consisting of" means including only those ingredients which follow the term as well as minor amounts of inactive additives or adjuvants;

"consisting essentially of" means including only the listed ingredients, minor amounts (less than 2%, 1%, 0.5%, 0.25%, or 0.1%, all w/v) of other ingredients that supplement the antimicrobial activity and/or provide a secondary effect (e.g., antifogging, soil removal, wound cleaning, etc.) that is desirable in view of the intended end use, and/or inactive additives or adjuvants;

"microbe" means any type of microorganism including, but not limited to, bacteria, viruses, fungi, viroids, prions, and the like;

"antimicrobial agent" means a substance having the ability to cause greater than a 90% (1 log) reduction in the number of one or more of microbes;

"active antimicrobial agent" means an antimicrobial agent that is effective only or primarily during the active parts of a microbe's lifecycle, e.g., cell division, and the activity of which involves disruption of a cellular process;

"biofilm" means a community of microbes, particularly bacteria and fungi, attached to a surface with the community members being contained in and/or protected by a self-generated macromolecular matrix;

"entrenched biofilm" means a biofilm that has reached a steady state mass after a growth period of two or more days;

"buffer" means a compound or mixture of compounds having an ability to maintain the pH of a solution to which it is added within relatively narrow limits;

"buffer precursor" means a compound that, when added to a mixture containing an acid or a base, results in a buffer;

"polyacid" means a compound having at least two carboxyl groups and specifically includes dicarboxylic acids, tricarboxylic acids, etc.;

"solvate" means the process of taking a solid material into solution in a liquid;

"sequestering agent" means a chemical that assists in solvating a compound and in preventing the solvated form of that compound from coming out of solution;

"metal ion sequestering agent" means a sequestering agent that works in connection with one or more metal ions, particularly alkali and alkaline earth metals;

"chronic otitis media" means otitis media with effusion or recurrent otitis media;

"soil load" means a solution of one or more organic and/or inorganic substances added to the suspension of a test organism to simulate the presence of body secretions, excretions, and the like;

"inoculum" means a solution containing bacteria, growth solution (e.g., tryptic soy broth) and protein soil load; and "substituted" (in reference to a functional group) means containing a heteroatom or functionality (e.g., hydrocarbyl group) that does not interfere with the intended purpose of the group in question.

"dwell time" means the amount of time that an antimicrobial agent is allowed to contact a bacterial biofilm;

"biocompatible" means presenting no significant, long-term deleterious effects on or in a mammalian species;

"ciliotoxic" means resulting in significant cleavage or loss of function of cilia; and "ciliacompatible" means not ciliotoxic.

Hereinthroughout, pH values of a liquid are those which can be obtained from any of a variety of potentiometric techniques employing a properly calibrated electrode, and effective solute concentrations preferably are determined by latent heat of fusion calculations from a properly calibrated DSC unit-produced scan acquired over a temperature range that includes the melting temperature of a given liquid composition.

Any numerical limitation used herein includes an appropriate degree of uncertainty based on the number of significant places used with that particular numerical limitation. For example, "up to 5.0" can be read as setting a lower absolute ceiling than "up to 5."

DETAILED DESCRIPTION

Compositions such as those summarily described in the preceding section can be used to break down, remove and/or disrupt biofilms including, advantageously, bacterial biofilms located in the middle or inner ear or the sinus cavities of an animal, particularly a mammal. The compositions are biocompatible and safe to use in and around the delicate tissues and structures of those areas because they are free of constituent materials which might harm such tissues or structures or unduly compromise long-term hearing.

Embodiments of the composition have a sufficiently low viscosity to enable delivery using techniques such as spray application, lavage, misting, mopping, wicking and dripping. These and other embodiments of the composition also can be easily removed from the treatment site by subsequent flushing, rinsing, and draining, although many such embodiments are sufficiently biocompatible to allow for absorption.

While not wishing to be bound by theory, a metal ion sequestering agent in the composition might complex or otherwise bond with metal ions which crosslink, bridge or otherwise assist in binding together polymer chains in the EPS/ECPS matrix of a biofilm. Other components of the composition then might surround the unbound polymer chains or fragments, breaking down the matrix, solvating the uncrosslinked polymer chains or fragments, and bringing them into solution or suspension so that they can be flushed or otherwise removed from the treatment area using, for example, additional amounts of the solvating system or a separate rinsing agent.

The composition includes solvent and solute components.

The solvent component of the composition includes water and at least one non-aqueous liquid.

Water has a high solute holding capability, good wetting properties, excellent biocompatibility, environmental friendliness, and low cost. Essentially any source of water can be used, although those that are relatively free of bacteria without advance treatment are preferred. The water need not be distilled, deionized, or the like, although such treatments certainly are not excluded, particularly where the water employed might include undesirable solutes which might interfere with the intended purpose of the composition. To enhance solubility of one or more of the other components of the composition, the water can be heated.

The one or more non-aqueous liquids typically has/have a $\delta_p$ value no higher than that of water, where $\delta_p$ is the dipolar intermolecular force (polarity) Hansen Solubility Parameter (HSP), a common method for predicting whether one material will dissolve in another to form a solution; the HSP values for most commonly used solvents are well documented.

Each component in a mixture or composition has three HSPs: dispersion, dipole-dipole (polarity) interactions, and hydrogen bonding. These parameters are generally treated as coordinates in three dimensions, with HSP characterizations being visualized using a spherical representation: the 3D coordinates are at the center of the sphere with the radius of the sphere ($R_0$ or "interaction radius") indicating the maximum difference in affinity tolerable for a "good" interaction with a solvent or solute. In other words, acceptable solvents lie within the interaction radius, while unacceptable ones lie outside it.

The distance between the HSPs of two materials in so-called Hansen space ($R_a$) can be calculated according to the following formula:

$$(R_a)^2 = 4(\delta_{d2}-\delta_{d1})^2 + (\delta_{p2}-\delta_{p1})^2 + (\delta_{h2}-\delta_{h1})^2 \qquad (I)$$

where $\delta_d$ is the energy from dispersion forces between the molecules, $\delta_p$ is the energy from dipole-dipole intermolecular forces, and $\delta_h$ is the energy from hydrogen bonds between molecules.

A simple composite affinity parameter, the Relative Energy Difference (RED), represents the ratio of the calculated HSP difference ($R_a$) to the interaction radius ($R_0$), i.e., RED=$R_a/R_0$. In situations where RED <1.0, the solubilities of the molecules are sufficiently similar that one will dissolve in the other. In situations where RED ≥1.0, the solubilities of the molecules are not sufficiently similar for one to dissolve the other. In situations where RED=1.0, partial dissolution is possible.

The dipole-dipole interaction Hansen solubility parameter for a particular solution or mixture of solvents can be calculated according to the following formula:

$$\delta_p = \sum_{i=1}^{n}(\delta_{di} \times x_{di}) \qquad (II)$$

where $\delta_{di}$ is the energy from dipolar intermolecular force for solvent i, $x_{di}$ is the percentage of solvent i in the solvent portion of the composition, and n is the total number of solvent components.

Hereinthroughout, the $\delta_p$ value for a given solvent or combination of solvents is determined at room temperature (because solubility typically increases with increasing temperature, meaning that the dissolution rate of the macromolecular matrix and the bacterial cell wall proteins will increase, the efficacy of the inventive composition is expected to increase at higher temperatures) and pH values are those which can be obtained from any of a variety of potentiometric techniques employing a properly calibrated electrode.

More details about HSPs and related concepts can be found US Pat. Publ. No. 2016/0073628.

The solvent component of the composition includes at least one non-aqueous liquid, typically one with a $\delta_p$ value no higher than that of water ($\delta_p \approx 16.0$ MPa$^{1/2}$). Exemplary composition intended for use in a sinus application can employ 5-20% (w/v) dimethyl sulfoxide (DMSO) with an overall $\delta_p \approx 16.0$ MPa, while exemplary compositions intended for use in an optic application can employ 5-15% (w/v) ethanol with an overall $\delta_p \approx 15.4$ MPa$^2$.

In certain embodiments, preference can be given to those organic compounds which are, or can be made to be, highly soluble in water and to those which are ciliacompatible. Additionally, preference can be given to any organic liquid that has been deemed to be safe and "inactive" (by regulatory bodies) at intended usage levels.

The composition includes at least 2% (w/v) of one or more non-aqueous (organic) liquids, with the upper limit determined in large part by the intended end use of the composition, i.e., the upper limit for sinus applications probably is higher than that for otic applications. In some embodiments, the lower limit can be 2.1, 2.2, 2.3, 2.4 or even 2.5%, with all of the foregoing being presented in w/v format. Exemplary ranges include 2.25-15% (sinus) or 2.0-10% (otic), with typical ranges being 2.5-13% (sinus) and 2.1-9% (otic) and preferred ranges being 2.5-12.5% (sinus) and 2.2-8% (otic), again with all of the forgoing being presented in w/v format.

In addition to the solvent component, the composition also includes as a primary component a solute component which can contain as few as two sub-components: the dissociation product(s) of at least one metal ion sequestering agent and at least one effective enzyme. In embodiments not intended for otic applications, anionic surfactant also can be included. The dissociation product(s) of one or more salts also can be included to increase effective solute concentration. Each of the foregoing ingredients generally is considered to be biocompatible.

The metal ion sequestering agent can be an acid or base capable of complexing or otherwise reacting with one or more metal ions in the EPS/ECPS matrix of a biofilm. Metal ions of particular interest, due to their likely involvement in the targeted biofilms, include sodium, calcium and iron. The metal ion sequestering agent desirably is water soluble, nontoxic and not prone to aggravate long-term hearing loss.

Acids generally are preferred over bases, although either type of sequestering agent can be used. Preference can be given to those metal ion sequestering agents which are biocompatible. Alternatively or additionally, preference can be given to those metal ion sequestering agents which can act to chelate the metallic cations ionic involved in cross-linking the macromolecular matrix of a biofilm. The metal ion sequestering agent preferably is not considered to be an oxidizer, particularly if it is an acid. Additionally, strong preference can be given to those acids and bases that have been deemed to be safe or "inactive" (by regulatory bodies) at intended usage levels Acidity is achieved by adding to water (or vice versa) one or more acids, specifically strong (mineral) acids such as HCl, $H_2SO_4$, $H_3PO_4$, $HNO_3$, $H_3BO_3$, and the like or, preferably, weak acids, particularly organic acids and, preferably, organic polyacids. Examples of organic acids include monoprotic acids such as formic acid, acetic acid and substituted variants, propanoic acid and substituted variants (e.g., lactic acid, pyruvic acid, and the like), any of a variety of benzoic acids (e.g., mandelic acid, chloromandelic acid, salicylic acid, and the like), glucuronic acid, and the like; diprotic acids such as oxalic acid and substituted variants (including oxamic acid), butanedioic acid and substituted variants (e.g., malic acid, aspartic acid, tartaric acid, citramalic acid, and the like), pentanedioic acid and substituted variants (e.g., glutamic acid, 2-ketoglutaric acid, and the like), hexanedioic acid and substituted variants (e.g., mucic acid), butenedioic acid (both cis and trans isomers), iminodiacetic acid, phthalic acid, ketopimelic acid, and the like; triprotic acids such as citric acid, 2-methylpropane-1,2,3-tricarboxylic acid, benzenetricarboxylic acid, nitrilotriacetic acid, and the like; tetraprotic acids such as prehnitic acid, pyromellitic acid, and the like; and even higher degree acids (e.g., penta-, hexa-, heptaprotic, etc.). Where a tri-, tetra-, or higher acid is used, one or more of the carboxyl protons can be replaced by cationic atoms or groups (e.g., alkali metal ions), which can be the same or different. Preferred acids include mono-, di- or tri-protic citric acid, acetic acid, octanoic acid and glutamic acid.

Basicity is achieved by adding to water (or vice versa) one or more bases such as, but not limited to, alkali metal salts of weak acids including acetates, fulmates, lactates, phosphates, and glutamates; alkali metal nitrates; alkali metal hydroxides, in particular NaOH and KOH; alkali earth metal hydroxides, in particular $Mg(OH)_2$; alkali metal borates; $NH_3$; and alkali metal hypochlorites (e.g., NaClO) and bicarbonates (e.g., $NaHCO_3$). Again, preference is given to those compounds which are, or can be made to be, soluble in water and which are biocompatible.

The concentration of metal ion sequestering agent added to water, or vice versa, is relatively unimportant because of the targeted effective solute concentration and hydronium ion concentration, i.e., 6≤pH≤8. Thus, use of a strong acid or base militates against addition of large amounts of that acid/base. Additionally, the relatively moderate effective solute concentration limits (discussed below) argue against significant amounts of buffer precursor. Conversely, use of a very weak acid or base permits addition of a much larger amount of the acid/base and/or a much reduced amount of a buffer precursor.

Each of U.S. Pat. Nos. 8,940,792 and 9,314,017, as well as U.S. Pat. Publ. Nos. 2010/0086576, 2014/0242188, and 2016/0073628, suggests that a decrease or increase (depending on whether an acid or base is used) in pH generally corresponds with enhanced efficacy. However, because the present composition is desired to be biocompatible and have minimal ciliotoxicity, the targeted pH range is one log unit either side of neutral. Thus, a key efficacy-enhancing variable from those prior teachings is not available in compositions of the present invention. The present composition has a targeted pH (t) which generally is on the order of t=6.5±v or t=7.5±v where v represents 0.4, 0.3, 0.25, 0.2, 0.15, 0.1 or 0.05.

The amount(s) of acid(s) or base(s) necessary to reach a given t value will, of course, depend on the strength of the particular acid(s) or base(s) used. Because even small amounts of those compounds considered to be weak acids or bases will adjust a composition's pH, respectively, below or above the aforementioned t values, the solute component almost always includes sufficient amounts of a buffer precursor (discussed below) so as to provide a composition having a desired t.

In addition to metal ion sequestering agent, each of the documents set forth in the preceding paragraph requires moderate-to-high levels of one or more surfactants. Because the compositions of the present invention are intended to be used in the presence of cilia and because many types of surfactant are known to be ciliotoxic, inclusion of surfactants is contraindicated. For embodiments of the composition intended for otic applications, this means that separately added surfactants are avoided altogether or strictly limited (e.g., less than 0.5, 0.41, 0.33, 0.25, 0.21, 0.17, 0.13, 0.09 or 0.05%, all w/v), while very limited amounts of one or more anionic surfactants can be included in embodiments intended for sinus applications. Again, this means that an efficacy-enhancing option from the aforementioned prior teachings is not available (or much less available) in compositions of the present invention The amount of anionic surfactant to be included in embodiments intended for use in sinus-related applications generally is less than 1.0%, commonly less than 0.75%, typically less than 0.5%, preferably less than 0.4%, more preferably less than 0.35%, and most preferably less than 0.3%, all presented in w/v format. Where one or more anionic surfactant(s) is/are included in a sinus-targeted composition, the total amount present generally is from 0.02 to 0.67%, commonly from 0.03 to 0.55%, typically from 0.04 to 0.42%, preferably from 0.05 to 0.39%, even more preferably from 0.06 to 0.36%, and still more preferably from 0.08 to 0.33%, all again w/v.

Potentially useful anionic surfactants include, but are not limited to, sodium chenodeoxycholate, N-lauroylsarcosine sodium salt, lithium dodecyl sulfate, 1-octanesulfonic acid sodium salt, sodium cholate hydrate, sodium deoxycholate, sodium dodecyl sulfate, sodium glycodeoxycholate, sodium lauryl sulfate, and the alkyl phosphates set forth in U.S. Pat. No. 6,610,314.

The enzyme sub-component of the solute component can be any one or more which is/are capable of facilitating microbial cell wall rupture by catalyzing and/or easing the breaking of chemical bonds present in or between molecules in those cell walls. One category believed to be particularly effective is glycosidase, particularly the species lysozyme. Testing to date has shown that lysozyme exhibits some efficacy at amounts as low as 80 ppm, i.e., 0.08 g lysozyme per kg of composition. Commonly employed amounts of enzyme(s) are at least 100 ppm, at least 125 ppm, and at least 150 ppm. Exemplary ranges include 85 to 500 ppm, 90 to 450 ppm, 95 to 400 ppm, 100 to 350 ppm, 105 to 300 ppm, 110 to 275 ppm, 115 to 250 ppm, 120 to 225 ppm, 125 to 200 ppm, 130 to 190 ppm, 135 to 185 ppm, and 140 to 180 ppm.

Composition efficacy generally increases with the presence of at least moderate effective solute concentrations, which generally increases in proportion with the amounts of solute subcomponents employed. However, the amounts of two of those subcomponents—metal ion sequestering agent and surfactant—are severely limited.

To increase the effective solute concentration (tonicity) of a composition, one or more types of other water soluble compounds can be included in the solute component. Such compounds, upon dissociation, increase the effective amount of solutes in the composition without greatly impacting the molar concentration of hydronium and hydroxyl ions.

Effective solute concentration of a composition can be increased by adding large amounts of ionic compounds, particularly electrolytes; see, e.g., U.S. Pat. No. 7,090,882. Essentially any compound that at least partially dissociates in water and/or the organic liquid(s) employed in the solvent component can be used to achieve this effect, with exemplary compounds including, but not being limited to, phosphates, acetates and any material deemed to be an "inactive ingredient" in injections, gels, creams, lotions, and/or ointments by governmental regulatory bodies.

A preferred method of increasing composition tonicity is employing a buffer precursor as a subcomponent of the solute component. For example, where the solute component includes one or more acids, one or more salts of those or other acids can be employed as solute subcomponent(s) which, in addition to increasing tonicity of the composition, provides a pH buffer to it. Where x moles of an acid are employed as a subcomponent of the solute component, an excess (e.g., 2x-8x) of one or more salts of that acid can be included as a separate subcomponent. (The same is true for basic compositions, mutatis mutandis.) The identity of the countercation of the acid salt (or counteranion of the base salt) is not particularly important. Where the salt of a polyacid is used as a buffer precursor, all or fewer than all of the carboxyl hydrogen atoms can be replaced; for example, mono-, di- and trisodium citrate all constitute potentially useful buffer precursors but the latter provides a greater theoretical buffering capacity than either of the other two. (Again, the same is true for salts of a polybase, mutatis mutandis.)

Regardless of how achieved, the tonicity of the composition is moderately high, with an effective solute concentration of from 100 to 300 mOsm/L being common and 200±10 mOsm/L being typical. Embodiments of the composition can exhibit minimum solute concentrations of 105, 110, 115, 120, 125, 130, 135, 140, 145, 150, 155, 160, 165, 170, 175 or 180 mOsm/L and maximum solute concentrations of 275, 260, 250, 245, 240, 235, 230, 225, 220, 215, 210, 205, 200, 195, 190 or 185 mOsm/L. Ranges based on each of the minimums and each of the maximums are envisioned, with some exemplary options including, but not being limited to, 110 to 275, 125 to 250, 150 to 250, 160 to 240, 160 to 225, 175 to 250, 170 to 240, 170 to 230, 180 to 240, 180 to 235, and 180 to 220 mOsm/L.

Although unnecessary and typically contraindicated, any of a variety of additives and adjuvants can be included in the solute component to make a composition more amenable for use in a particular end-use application with negatively affecting its efficacy in a substantial manner. Examples include, but are not limited to, fragrances, pigments, dyes, essential oils, foaming agents, flavors, preservatives (e.g., antioxidants) and the like.

The solute component thus provides to the composition a near-neutral pH, typically from 6 to 8, and a moderate amount of osmotically active solutes, often having an effective solute concentration of no more than 250 mOsm/L and commonly no more than 200 mOsm/L. Some embodiments include no more than 0.5% (w/v) of one or more anionic surfactants, while others include no added surfactant(s). The composition also includes a relatively small amount of one or more effective enzymes. The foregoing can be tabulated as set forth below, with any value in a given row being combinable with any value for each of the other subcomponent:

TABLE 1a otic compositions
Solute subcomponents

| | |
|---|---|
| metal ion sequestering agent(s), g/L | 0.05-100, 0.1-50, 0.15-25, 0.2-10, 0.5-5 |
| surfactant, g/L | <2.5, <2, <1.5, <1, <0.5, ~0 |
| enzyme, ppm | 60 to 400, 100 to 300, 125 to 250, 150 to 225 |
| other, including salts of sequestering agent(s), g/L | 0.5-100, 0.6-75, 0.7-50, 0.8-30, 1-25 |
| Tonicity, mOsm/L | 100-275, 125-250, 150-225, 175-220 |
| $C_2$-$C_4$ alcohol, % (v/v) | 1.8-10, 2.0-9, 2.1-8, 2.2-7, 2.3-6 |

TABLE 1b sinus compositions
Solute subcomponents

| | |
|---|---|
| metal ion sequestering agent(s), g/L | same as otic |
| surfactant, g/L | 3-75, 6-70, 10-65, 12-60, 15-56 |
| enzyme, ppm | same as otic |
| other, including salts of sequestering agent(s), g/L | 0.5-150, 1-125, 1.5-100, 2-75, 3-50 |
| Tonicity, mOsm/L | same as otic |
| DMSO, % (v/v) | 2.0-20, 2.2-17, 2.3-15, 2.4-13, 2.5-12.5 |

Various embodiments of the present invention have been provided by way of example and not limitation. As evident from the foregoing tables, general preferences regarding features, ranges, numerical limitations and embodiments are to the extent feasible, as long as not interfering or incompatible, envisioned as being capable of being combined with other such generally preferred features, ranges, numerical limitations and embodiments.

The composition can be prepared in a number of ways. Description of an exemplary method follows.

Each of the solute subcomponents other than the enzyme(s) can be added to sufficient water to constitute 60-90% of the calculated desired volume. This solution can be stirred and/or heated if desired. The desired amount of organic liquid(s) and enzyme(s) then can be added. Once stirring, if used, is complete, sufficient water is added so as to bring the composition to the calculated tonicity and pH value. Advantageously, no special conditions or containers are needed to store the composition for an extended time, although refrigeration can be used if desired.

The composition conveniently can be provided as a solution, although other forms might be desirable for certain end-use applications. Accordingly, the composition can provided as a soluble powder (for subsequent dilution, an option which can reduce transportation costs), a slurry or emulsion, or a thicker form such as a gel (including hydrogels, organogels and xerogels) or paste (i.e., a suspension in an organic base such as a fatty acid), either of which might be particularly useful for providing increased residence times. For the latter, the composition can include additional ingredients such as a coalescent (e.g., polyvinylpyrrolidone). Salves or ointments, aerosols, foams, and even suspensions also are possible.

An advantage of the composition described herein is an ability to detach biofilms from the tissues to which they are attached. Regardless of whether this occurs, the composition can significantly reduce the number of viable bacteria remaining on or around the affected tissue.

Even where use of a composition does not result in detachment of a biofilm, embodiments of the composition can provide large reductions in the number of bacteria, even with extremely short residence times. For example, a 1, 2, 3 or 4 log (99.99%) reduction in the number of bacteria in an entrenched biofilm with a 3, 4, 5, 7, 8, 9, or 10 minute residence time is possible.

The composition can act at least in part to interrupt or break ionic crosslinks in the macromolecular matrix of a biofilm, facilitating the passage of solutes and surfactant through the matrix to bacteria entrained therein and/or protected thereby. Disruption of the macromolecular matrix advantageously also can result in detachment of the biofilm, alternatively or in addition to treating bacteria entrained in that matrix.

The majority of the foregoing discussion has centered on biofilms, particularly bacterial biofilms. This is unsurprising given that a majority of sinus and otic issues have a bacterial origin. However, the composition exhibits efficacy against bacterial forms other than biofilms and against microbes other than bacteria. Advantageously, the composition can kill and/or prevent growth of microbes, regardless of their phase of life cycle.

With respect to bacteria, each of the lag phase (metabolic protein production), log phase (reproduction) and stationary phase (approximately equal amounts of dying, metabolizing and reproducing bacteria) of a bacterium's lifecycle technically constitutes an "active" phase. Regardless of whether an individual bacterium is dormant, reproducing, or metabolizing, the composition can kill it or prevent it from growing.

Bacteria that are part of biofilms often are dormant (not metabolizing or reproducing), and this lack of cellular processes (inactivity) often provides resistance to antibiotics, which require active metabolism or reproduction for efficacy, and other active antimicrobials.

Viruses technically are not living microbes because they require a host for reproduction. Nevertheless, the composition is capable of disrupting, penetrating and/or dissolving the protein coating(s) on a virus. The ability to attack these protective structures means that the composition exhibits efficacy against a virus before it ever achieves the ability to reproduce after cellular infection.

Ciliotoxicity generally increases with increasing surfactant concentration, increasing tonicity, and/or departure of pH from neutral. Given the foregoing description, the ordinarily skilled artisan can provide a ciliacompatible composition that remains effective against microbes in biofilm form.

The composition can be employed in a variety of ways.

For otic applications, it can be delivered to the targeted areas of the ear during and/or after surgery. This might be as simple as washing or rinsing the outer surface of a tympanic membrane, for example, one on which a surgical procedure is to be performed. (In such cases where the composition is not expected to pass the tympanic membrane, a composition with more aggressive pH and tonicity values can be employed.) For procedures involving access of the middle/inner ear, the composition can be delivered through a tympanostomy tube or via syringe inserted through a perforation or incision in the tympanic membrane. In both cases, a medical professional can continue to insert composition until liquid backflow is observed. (A typical human middle ear holds 1 to 1.5 mL of liquid, by way of example.)

For sinus applications, the composition can be introduced to the sinus cavity via a surgical technique such as trephination or via a remote delivery mechanism such as, e.g., a Hydrodebrider™ endoscopic sinus irrigation system (Medtronic; Minneapolis, Minn.) or a Relieva Vortex™ sinus irrigation catheter (Acclarent, Inc.; Irvine, Calif.). Regardless of delivery mechanism, a medical profession can continue delivering composition to the targeted cavity(ies) until returning effluent appears visually clear.

Regardless of where used, the composition can be permitted a dwell of time of a few seconds up to several hours. The targeted dwell time typically depends on the nature of the patient (e.g., ability to be sufficiently immobile to permit a long dwell time) as well as the physiology of the area to be treated, e.g., whether liquid introduced to that area naturally drains or pools.

As mentioned previously, flushing or rinsing of the treated area typically is not necessary, although irrigation with a liquid such as a normal saline solution certainly is possible.

The antimicrobial composition also or alternatively can be used to provide sterility to pre- and post-surgical articles such as sponges, topical wipes, bandages, pads, gauze, surgical packing, and the like, particularly those intended or expected to contact cilia-containing tissue.

Although sterilized, medical device implants such as tympanostomy tubes can become colonized, prior to and during implantation, with bacteria from the environment, from a healthcare worker, or more commonly from bacteria present on the patient's own skin. After insertion, these implants can become colonized from systemic bacteria which make their way to the implant which provides a surface for biofilm growth because the implant surface is not protected by the host immune defenses. In addition, currently employed sterilization techniques are not designed to remove EPS/ECPS, the presence of which greatly facilitates formation of a biofilm; therefore, even a sterilized device/article that is properly implanted can have EPS/ECPS on its surface from previous exposure.

If a biofilm forms on an implant, no currently available treatment can eradicate it. Systemic antibiotics are ineffective against such infections, certainly due to the inherent protection by the EPS/ECPS but also perhaps due to limited blood supply at the surface of the implanted article.

The aforedescribed antimicrobial compositions can be effective topical treatments, applied to a to-be-implanted device or article or can be used to wash the infected implant and surrounding tissue to rid the body of a biofilm and/or biofilm-forming materials such as EPS/ECPS.

The tympanic membrane where the implant is or was located likewise can be treated with the previously described composition. This can be done at the time of the original implantation (i.e., immediately following insertion of the article), and can be followed with rinsing/irrigation, suctioning or both.

As has been mentioned several places above, deciliation is a significant concern for any composition that is intended for use in the sinus cavities and, particularly, the middle-inner ear. While deciliation is preferably avoided altogether, no more than ~20%, preferably no more than ~15%, and more preferably no more than ~10%, is acceptable for compositions intended for use in sinus applications. For otic compositions, the acceptable upper limit is that which results in measurable hearing loss. Deciliation can be determined via scanning electron microscopy, as described more fully below, and/or audiometric testing.

The relevant portions of any specifically referenced patent and/or published patent application are incorporated herein by reference.

EXAMPLES

The relative efficacy of treating compositions was determined using a MBEC high throughput screening assay, similar to that used in the procedure described in ASTM E2799-12 (Standard Test Method for Testing Disinfectant Efficacy against *Pseudomonas aeruginosa* Biofilm Using the MBEC Assay). The assay employed a multiwell assembly 10 of the type shown in FIG. 1, which includes plate 12 having multiple wells 14 and lid 16 having multiple pegs 18. Each of plate 12 and lid 16 is made of a plastic such as polystyrene or polycarbonate.

Figure 2:
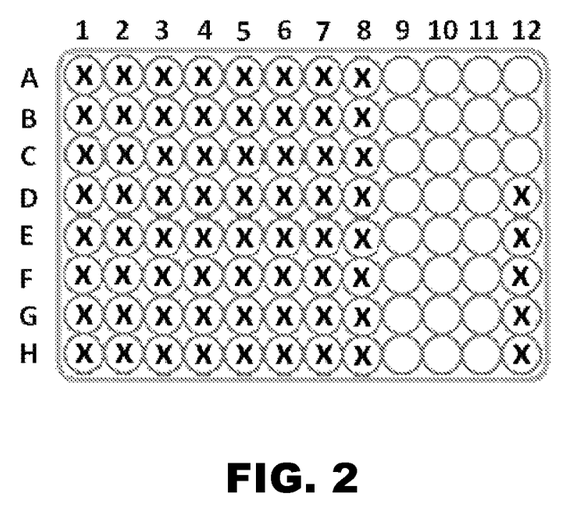
FIG. 2 is a top view of an 8×12 multiwell array employed in the testing of treating compositions of the present invention.

Bacteria is propagated in one or more of multiple wells 14 immediately after a plate 12 is removed from sterile packaging. In the following examples, the plate included 96 wells in an array of 8 rows and 12 columns, as graphically represented in FIG. 2. Each of 69 of the wells designated with an X received 150 μL of the $10^5$ dilution inoculum. None of the wells in columns 9-11 were used, while wells A12-C12 were reserved for use as sterility controls. The five wells represented by D12-H12 served as bacterial growth controls.

The bacteria used were *S. aureus*, ATCC 33592 (MRSA), and *P. aeruginosa*, ATCC 15442. The surface of appropriate agar media were inoculated with a recently grown stock culture of each bacteria. An isolated colony was aseptically removed from the plate and inoculated with 200 mL of soybean-casein digest medium; flasks were incubated at 350±2° C. and 150±10 rpm (18-24 hours for staph, 16-18 hours for *Pseudomonas*) with viable bacterial densities being targeted at ≥$10^8$ CFU/mL, checked by serial dilution and plating. Into 100 mL portions of the growth medium were pipetted 10 μL aliquots from each incubation flask, so as to adjust the bacterial densities to $10^5$ CFU/mL; these were vortexed to achieve homogeneous distributions. Ten-fold serial dilutions of the inoculums from the preceding sentence were performed in triplicate, with 20 μL aliquots of the serial dilutions being spot plated on appropriate agar plates from $10^0$-$10^7$ before incubating the plates at 350±2° C. (18-24 hours for staph, 16-18 hours for *Pseudomonas*).

Figure 1:
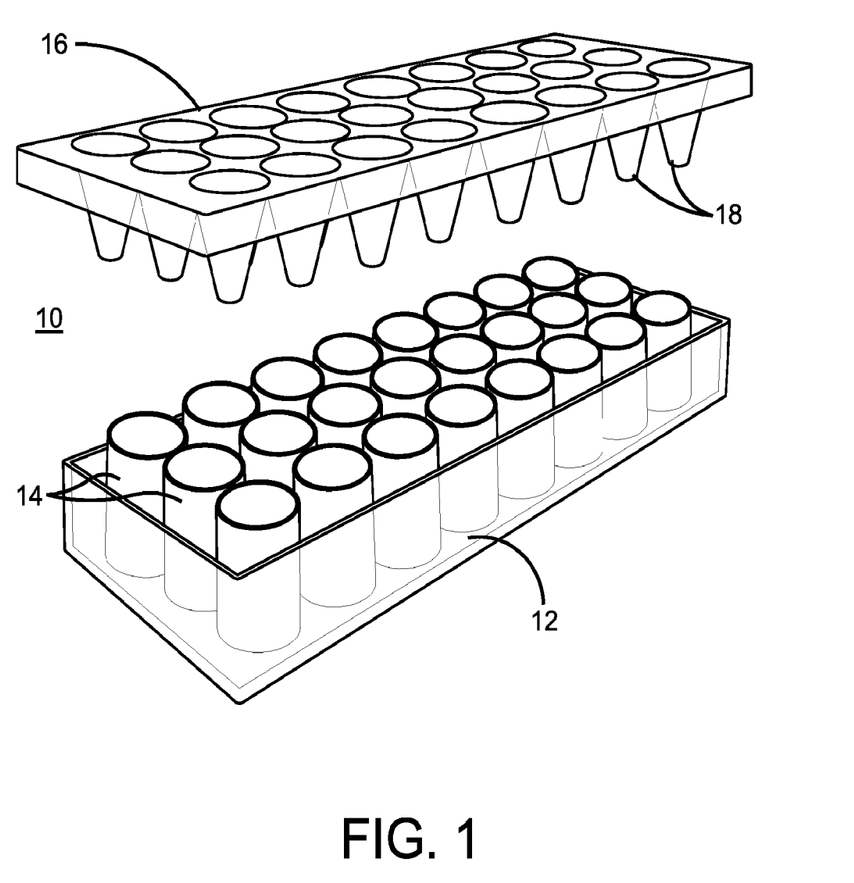
FIG. 1 is a perspective, schematic view of a disassembled simplified multiwell array, of the type employed in a minimum biofilm eradication concentration (MBEC) high throughput screening assay.

Lid 16 was placed on plate 12, and assembly 10 was labeled before being placed onto an orbital incubator/shaker set to 110±10 rpm. The incubator/shaker was allowed to run at 35°±2° C. for the amount of time noted previously as being appropriate for each bacterium type.

The bacterial growth pegs (D12-H12 in FIG. 2) were broken off using flame sterilized pliers held flush against lid 14. Each of those five pegs was placed into a separate sterile microcentrifuge tube with 1.0 mL phosphate-buffered saline (PBS). The microcentrifuge tubes then were placed on a stainless steel tray floated in the center of a sonication device; the tray was permitted to sonicate for 1800±300 seconds. After sonication, the solution in each microcentrifuge tube was serially diluted by transferring 0.1 mL into a new sterile microcentrifuge tube containing 0.9 mL PBS. The dilutions were spot plated onto agar appropriate for the particular bacterium being tested.

Figure 3:
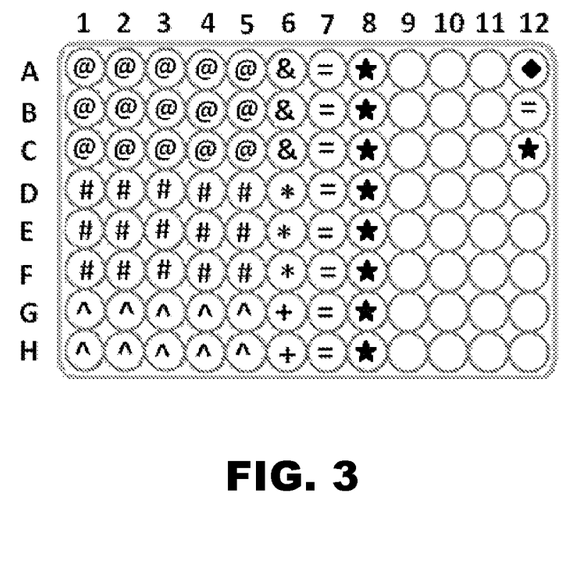
FIG. 3 is a top view of a challenge plate matrix employed in the testing of treating compositions of the present invention.

One plate, designated the "Challenge Plate," is graphically depicted in FIG. 3, where the symbols represent the following:

| | | | |
|---|---|---|---|
| @ | lysozyme-containing composition | ★ | PBS |
| # | lysozyme-free composition | & | 50:50 lysozyme-containing composition/ sterile neutralizer |
| ^ | saline | | |
| = | sterile neutralizer | * | 50:50 lysozyme-free composition/sterile neutralizer |
| ♦ | sterile broth | | |
| | | + | 50:50 saline/sterile neutralizer |

Into well A12 of that plate was added 200 μL sterile broth, with that well serving as the device sterility control. Next, 200 μL sterile neutralizer was added to each well in column 7 (neutralizer toxicity control) and well B12 (neutralizer sterility control), while the wells in column 6 (neutralizer effectiveness controls) received 100 μL sterile neutralizer followed by 100 μL of a test composition: lysozyme-containing composition in rows A-C, composition without lysozyme in rows D-F, and normal saline in rows G-H. To each well in column 8 (untreated control) and well C12 (PBS sterility control) was added 200 μL PBS. For columns 1-5, each well received 200 μL of a test composition: lysozyme-containing composition in rows A-C, composition without lysozyme in rows D-F, and normal saline in rows G-H.

The Challenge Plate was placed into a humidified incubator set at 360±1° C. for at least 60 minutes.

Also provided for each test was a Rinse Plate (200 μL PBS in each well), a Recovery Plate (200 μL sterile neutralizer in each well), and Quantification Plates 1-3 (100 μL sterile neutralizer in row A of each and 180 μL PBS in rows B-H of each).

The Challenge Plate was removed from the incubator. The Growth Plate peg lid was rinsed for ~10 seconds to remove any planktonic microbes and transferred onto the Challenge Plate before the combination was incubated at 360±1° C. for the appropriate time described above. Thereafter, the peg lid was transferred to the Recovery Plate.

From the Challenge Plate was transferred 100 μL of the contents from each well of row A into the corresponding row A well of the Quantification Plate 1, 100 μL of the contents from each well of row D into the corresponding row A well of the Quantification Plate 2, and 100 μL of the contents from each well of row G into the corresponding row A well of the Quantification Plate 3.

The Recovery Plate was placed in the stainless steel tray of the sonicating device and permitted to sonicate for 1800±300 seconds.

Dilution Plates 1-3 were prepared by adding 180 µL PBS into the wells of rows B-H of new 96-well multiwells. Following sonication, 100 µL of the contents from each well of row B of the Recovery Plate were transferred into the corresponding well of row A of Dilution Plate 1. Serial dilutions (100-10$^7$) were achieved by transferring 20 µL down each of the 8 rows, e.g., 20 µL from cell A1 was put into B1, diluted and mixed, 20 µL from cell B1 was put into C1, diluted and mixed, etc. The contents of each well of Dilution Plate 1 were mixed by pipetting up and down, with the pipette tip being discarded after mixing each row. The dilution series from the Dilution Plate 1 was spot plated on appropriate agar for viable cell counts, described below.

Similarly, 100 µL of the contents from each well of row E of the Recovery Plate were transferred into row A of Dilution Plate 2, and 100 µL of the contents from each well of row H of the Recovery Plate were transferred into row A of Dilution Plate 3. Dilution and spot plating for each were performed as with Dilution Plate 1.

Each of Quantification Plates 1-3 were treated similarly to Dilution Plates 1-3.

All agar plates were incubated at the appropriate temperature and for the appropriate time in view of the type of bacteria being tested.

Each plate was visually inspected, with any colony that was visibly distinct from other colonies being counted as a colony forming unit (CFU) and that number being used in the following formula to determine relative efficacies of compositions at various concentrations:

$$\log_{10}[10^x (CFU/V_{pl})(V_w/A_{pg})]$$

where $V_{pl}$ is the plated volume in µL, $V_w$ is the volume of a plate well (here, 200 µL), $A_{pg}$ is the area of a lid peg (here, 46.63 mm$^2$), and x is an integer representing the plate row, i.e., 1 for row A, 2 for row B, 3 for row C, etc. The average of the values for each of columns 1-5 were determined, and log reduction was determined by subtracting the average of treated pegs from the average of untreated pegs.

As confirmations, pegs A12-C12 were checked to ensure that they remained clear, pegs D12-H12 were checked to ensure the presence of 10$^4$-10$^6$ CFU/mm$^2$ of recovered microbe, column 6 was checked to ensure neutralizer effectiveness, column 7 was checked to ensure neutralizer non-toxicity, and column 8 was checked to ensure microbial growth.

Example 1: Otic Composition

Approximately 1 L of an exemplary solution for washing of the middle ear was prepared from the following combination of ingredients:
  0.8 g/L anhydrous citric acid,
  19.1 g/L trisodium citrate dihydrate,
  50 g/L ethanol, and
  0.15 g/L lysozyme.

The composition was calculated to have an effective solute concentration of ~200 mOsm/L, and its measured pH was 6.5.

When tested in a MBEC biofilm reactor, with a 5 minute static application time, this composition was shown to result in a 0.8 log reduction in *S. aureus* and a 2.2 log reduction in *P. aeruginosa*.

Example 2: Sinus Composition

Approximately 1 L of an exemplary solution for introduction into the sinuses was prepared from the following combination of ingredients:
  0.75 g/L anhydrous citric acid,
  14.25 g/L trisodium citrate dihydrate,
  100 g/L DMSO,
  0.15 g/L lysozyme, and
  5 g/L sodium lauryl sulfate.

The composition was calculated to have an effective solute concentration of ~200 mOsm/L, and its measured pH was 7.0.

When tested in a MBEC biofilm reactor, with a 5 minute static application time, this composition reduced *S. aureus* by 3 log.

Example 3: Ciliotoxicity Testing, Sinus—Human Sinonasal Epithelial Cells

The ALI model, which uses epithelial tissue grown on permeable filter supports submerged in culture medium, was used as a screening test to determine whether the composition employed in Example 2 exhibited significant ciliotoxicity.

Mucosal specimens acquired from residual clinical material obtained during sinonasal surgery were transported to the laboratory in saline placed on ice. ALI cultures were established from human sinonasal epithelial cells enzymatically dissociated human tissue using procedures described at, for example, M. Ramanathan et al., "A comparison of experimental methods in molecular chronic rhinosinusitis research." *Am. J. Rhinol.*, vol. 21, pp. 373-77 (2007).

Cultures were grown to confluence in tissue culture flasks (75 mL) with an appropriate proliferation medium before the epithelium was allowed to differentiate five days later.

Mucosal samples prepared according to the procedure described in M. B. Antunes et al., "Murine Nasal Septa for Respiratory Epithelial Air-Liquid Interface Cultures," *Bio-Techniques*, no. 43, pp. 195-204 (2007) were placed in a glass perfusion chamber.

Beating cilia on the edges of each sample were identified using a Leica DMLFSA microscope set on an air table, using a water immersion 63× objective and differential interference contrast optics (Leica Microsystems, Inc.; Bannockburn, Ill.). Once beating cilia were observed, two seconds of video at a sampling rate of 100 frames/second were captured with a high-speed monochromatic digital video camera (Basler AG; Ahrensburg, Germany), with the video images being routed into a PC workstation for compression and storage. This process was repeated at 1-minute intervals, with a 5-minute baseline beating rate being determined before 20 µL of the composition from Example 2 was pipetted onto the apical surface of the mucosal sample and video imaging was continued. Image files were analyzed with virtual instrumentation software customized to analyze ciliary beating. (For more information on this type of video image analysis technique, see J. H. Sisson et al., "All-digital image capture and whole-field analysis of ciliary beat frequency," *J. Microscopy*, vol. 211, pp. 103-11 (2003).)

The targeted result was a finding that at least 50% of cilia (as measured by active area) would continue beating through 30 minutes of exposure of a sample to the composition.

Figure 4:
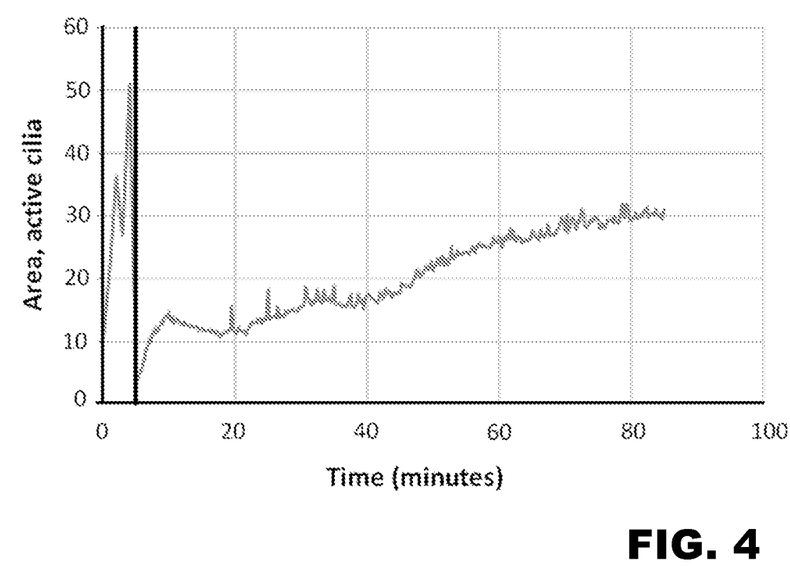
FIGS. 4 and 5 depict Air-Liquid Interface (ALI) model ciliotoxicity testing results for a sinus treatment composition, with active cilia area plotted against time in FIG. 4 and cilia beat frequency plotted against time in FIG. 5.

The actual results of the testing are shown in FIG. 4. The median active area for the baseline period was ~24.3%, while the median active area as measured at 30-33 minutes was ~16.4%. Accordingly, the treating composition from Example 2 was deemed to have passed the ALI screening test.

Figure 5:
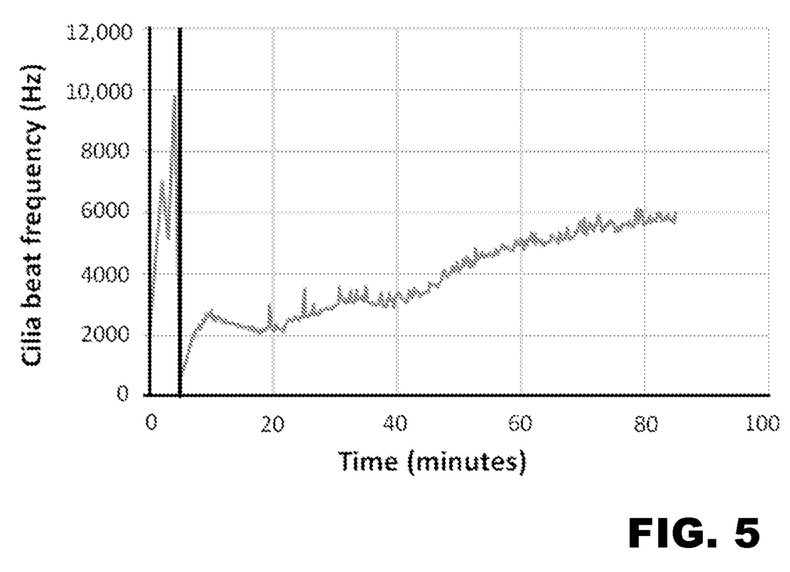

The beat frequency of the cilia during exposure to the treating composition from Example 2 also was measured, with those results being shown in FIG. 5. The median cilia beat frequency for the baseline testing was ~4670 Hz, while the median for the solution at 30-33 minutes of exposure was ~3160 Hz. FIG. 5 also indicates that cilia beat frequency continues to increase after exposure.

Example 4: Ciliotoxicity Testing, Sinus—Explant

The sinus treating composition from Example 2 also was tested on three harvested mouse nasal septa. (Harvesting was conducted as described in the M. B. Antunes et al. article mentioned previously.)

Each harvested septal explant was held in sterile PBS before being placed in a glass perfusion chamber held in place with a nylon grid (1.5 mm), the outer frame of which snapped into the inside of the perfusion chamber (Warner Instruments; Hamden, Conn.). Each explant was tested at 27.5° to 28.5° C.

A 3-minute baseline beating rate was determined before each explant sample was given a 3-minute exposure to the sinus treating composition from Example 2.

The video image analysis technique employed in Example 3 again was employed.

Tabulated below are the median cilia beat frequency for the baseline period and 27-30 minutes after exposure.

TABLE 2 cilia beat frequency of mouse explants (Hz)

| | Baseline | Post-exposure |
|---|---|---|
| sample 1 | 4.8 | 8.0 |
| sample 2 | 5.1 | 6.1 |
| sample 3 | 6.6 | 8.9 |

The cilia beat frequency values after exposure are greater than those before exposure, indicating no debilitating damage to the cilia of the explant samples.

Example 5: Ciliotoxicity Testing, Sinus—In Vivo

The sinus treating composition from Example 2 also was tested on ciliated mucosal surfaces in the sinuses of living rabbits at the University of Sao Paolo.

Using the procedure described in E. Tamashiro et al., "In vivo effects of citric acid/zwitterionic surfactant cleansing solution on rabbit sinus mucosa," *Am. J. of Rhinology & Allergy*, vol. 23, no. 6, pp. 597-601 (2009), indwelling catheters were placed into the maxillary sinuses of female New Zealand white rabbits, with 10 mL (at a rate of 0.33 mL/sec) of either 0.9% normal saline or the treating composition from Example 2 being instilled into the sinuses, followed by aspiration.

Test rabbits were anaesthetized and killed either one day or seven days after irrigation. The 7-day timeframe permits evaluation of possible long-term deciliation, while the 1-day timeframe guards against the possibility of immediate deciliation followed by regrowth in the intervening six days. (Sinus cilia often regrow within 48 hours of being lost.)

Mucosa from both left and right maxillary sinuses were harvested, with each mucosa sample being evaluated by scanning electron microscopy (SEM) for morphological integrity of the epithelium.

Analysis of the SEM images indicated the ciliotoxicity of the treating composition from Example 2 equivalent to or even less than that of normal saline, both after 1 day and after 7 days.

Example 6: Ciliotoxicity Testing, Middle Ear

Ototoxicity testing was conducted by the Department of Otolaryngology in the University of Florida College of Medicine, employing internally approved animal handling/testing procedures which conform to the National Institutes of Health *Guidelines for the Care and Use of Laboratory Animals*.

After an acclimation period of at least 5 days, each of eight mature, albino male guinea pigs (Charles River; Wilmington, Mass.) underwent a bilateral myringotomy, conducted with a blunt 27 gauge sterile needle. Sufficient liquid was injected so as to fill the animals' middle ear spaces (~0.2 mL), with one ear receiving a control 0.9% normal saline solution and the other receiving the treating composition from Example 1. After injection, the dorsal skull of each animal was tapped gently to ensure thorough exposure of the entireties of the animal's middle and inner ears to the liquids.

None of the test animals displayed evidence of vestibulopathy during the study.

Cochlear action potential for each animal was measured before solution injections, 7 days after injection, and 28 days after injection, using electrocochleography as described by T. M. Lo et al., "Hearing loss with stapedotomy and treated otitis media," *Otolayngol. Head Neck Surg.*, vol. 134(4), pp. 674-79 (April 2006). Electrocochleographic thresholds were measured for calibrated tone bursts generated by an auditory electrophysiology workstation using software from Tucker-Davis Technologies (Gainesville, Fla.) and electrostatic speakers. Stimuli were introduced through insert headphones placed in the animal's external auditory canal. Tone bursts at frequencies of 4 kHz, 8 kHz, 16 kHz and 24 kHz were presented. Beginning at 100 dB, auditory thresholds were evaluated by decreasing stimulus intensity in 5 dB decrements until disappearance of the waveform. Waveforms were averaged in response to 512 tone bursts at each tested frequency/amplitude combination.

Hearing thresholds for each ear were compared using a paired, two-tailed t-test (SAS Institute Inc.; Cary, N.C.). Significance levels were determined at $p<0.05$.

A significant hearing loss for these experiments was considered to be a 10 dB difference.

Figure 6:
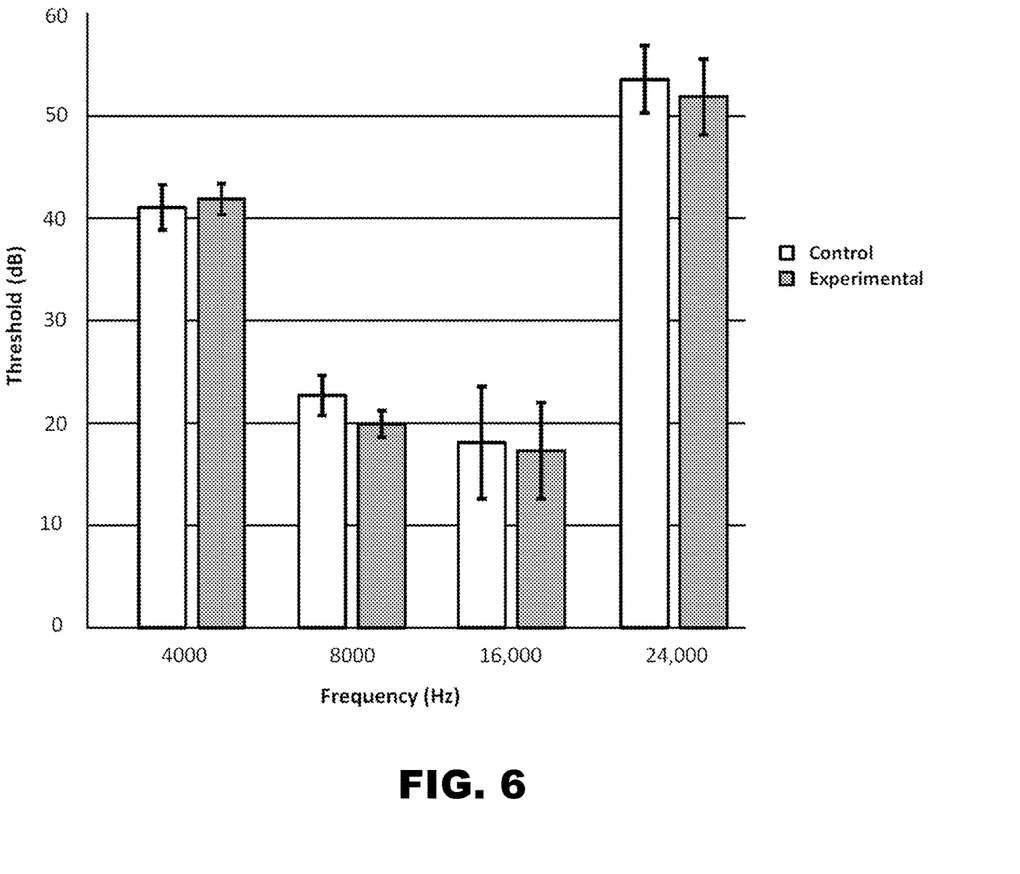
FIG. 6 depicts averaged baseline hearing threshold data for eight guinea pigs.
Figure 7:
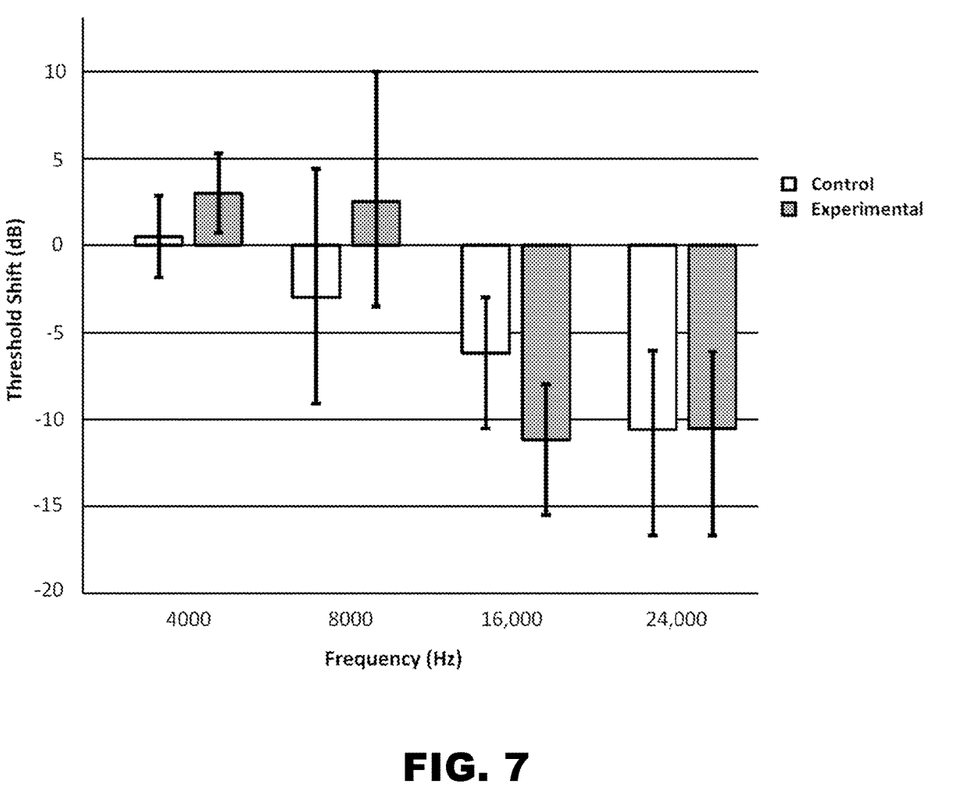
FIGS. 7 and 8 depict averaged threshold shifts in hearing for eight guinea pigs, with FIG. 7 being based on data collected 7 days after liquid insertion and FIG. 8 being based on data collected 28 days after liquid insertion.
Figure 8:
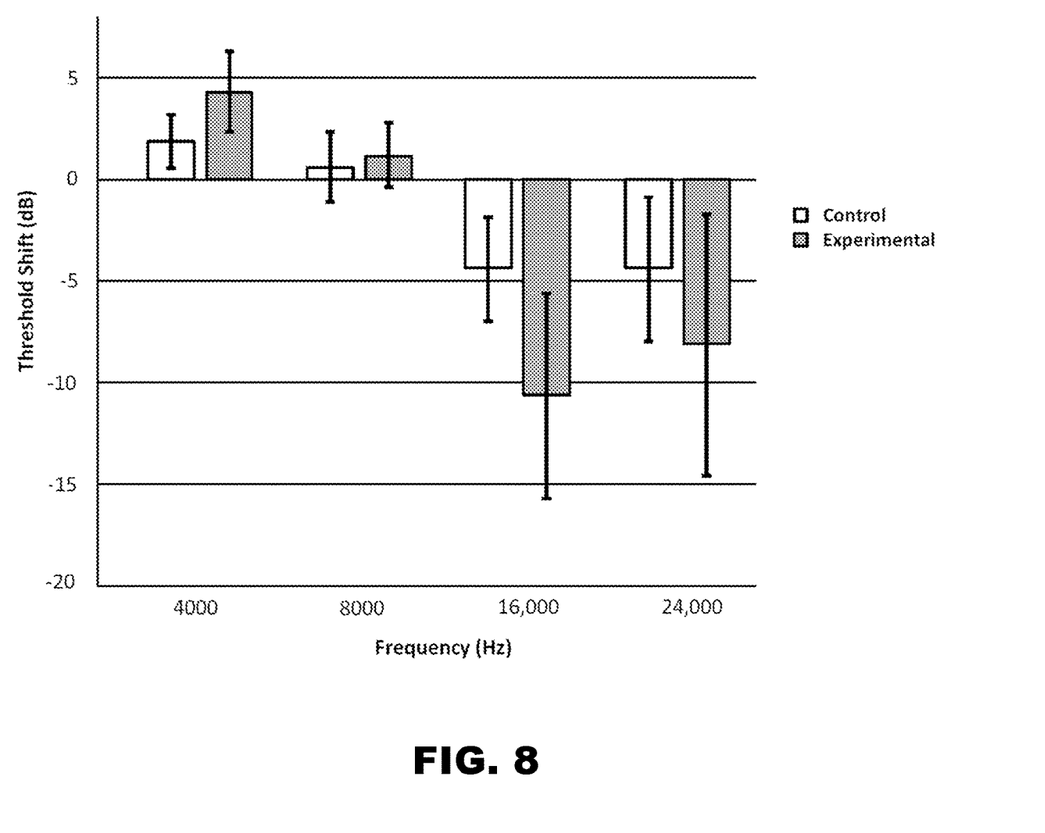

Averaged hearing thresholds for the test animals prior to injection of any liquids can be seen in FIG. 6, while averaged hearing threshold shifts for the test animals 7 days and 28 days after liquid injection can be seen in, respectively, FIGS. 7 and 8. (Bars represent standard error.)

In each case, hearing thresholds between treatments were not different at all frequencies ($p>0.05$).

After final hearing assessments, each animal was euthanized so that their cochlea could be examined by SEM so as to assess outer hair cell (OHC) loss. When possible the cochlea were imaged from all three turns, i.e., basal, middle and apical.

Thorough analysis of multiple images revealed no substantial difference in the OHC loss of the middle ears receiving the treating composition from Example 1 relative to the ears receiving the control saline solution.

Based on both the comparative hearing data and the SEM analysis, the report concluded that the treating composition employed in Example 1 did not cause ototoxicity. The results were deemed to be sufficiently definitive that a follow-on confirmative study employing chinchillas was recommended to be foregone.

That which is claimed is:

1. An antimicrobial composition suitable for introduction into cilia-containing areas of an animal body, said composition consisting essentially of:
   a) a solvent component that consists of water and at least 2% (w/v) of an organic solvent selected from ethanol and DMSO, and
   b) a solute component that consists of an organic polyacid, a salt of an organic polyacid, no more than 1% (w/v) of one or more anionic surfactants and at least 0.005% (w/v) of lysozyme, said composition having a pH of from 6 to 8 and an effective solute concentration of no more than 250 mOsm/L.

2. The composition of claim 1 wherein said composition has an effective solute concentration of no more than 200 mOsm/L.

3. The composition of claim 1 wherein said organic polyacid is citric acid.

4. The composition of claim 1 wherein said salt of an organic polyacid is a sodium salt of citric acid.

5. The composition of claim 1 wherein said solute component includes no more than 0.8% (w/v) of said one or more anionic surfactants.

6. The composition of claim 5 wherein said solute component includes no more than 0.7% (w/v) of said one or more anionic surfactants.

7. The composition of claim 6 wherein said solute component includes no more than 0.5% (w/v) of said one or more anionic surfactants.

8. The composition of claim 7 wherein said solute component is free of anionic surfactants.

9. The composition of claim 1 wherein said organic solvent is DMSO.

10. The composition of claim 1 wherein said organic solvent is ethanol.

11. An antimicrobial composition suitable for introduction into cilia-containing areas of an animal body, said composition consisting of:
   a) a solvent component that consists of water and at least 2% (w/v) of an organic solvent selected from ethanol and DMSO, and
   b) a solute component that consists of an organic polyacid, a salt of an organic polyacid, no more than 1% (w/v) of one or more anionic surfactants and at least 0.005% (w/v) of lysozyme, said composition having a pH of from 6 to 8 and an effective solute concentration of no more than 250 mOsm/L.

12. The composition of claim 11 wherein said composition has an effective solute concentration of no more than 200 mOsm/L.

13. The composition of claim 11 wherein said organic polyacid is citric acid.

14. The composition of claim 11 wherein said salt of an organic polyacid is a sodium salt of citric acid.

15. The composition of claim 11 wherein said solute component includes no more than 0.8% (w/v) of said one or more anionic surfactants.

16. The composition of claim 15 wherein said solute component includes no more than 0.8% (w/v) of said one or more anionic surfactants.

17. The composition of claim 16 wherein said solute component includes no more than 0.8% (w/v) of said one or more anionic surfactants.

18. The composition of claim 17 wherein said solute component is free of anionic surfactants.

19. The composition of claim 11 wherein said organic solvent is DMSO.

20. The composition of claim 11 wherein said organic solvent is ethanol.

* * * * *